(12) United States Patent
Yokoyama et al.

(10) Patent No.: US 6,779,159 B2
(45) Date of Patent: Aug. 17, 2004

(54) DEFECT INSPECTION METHOD AND DEFECT INSPECTION APPARATUS

(75) Inventors: Hirokazu Yokoyama, Osaka (JP); Yutaka Nakashima, Tokyo (JP)

(73) Assignee: Sumitomo Mitsubishi Silicon Corporation (JP)

( * ) Notice: Subject to any disclaimer, the term of this patent is extended or adjusted under 35 U.S.C. 154(b) by 77 days.

(21) Appl. No.: 10/156,464

(22) Filed: May 29, 2002

(65) Prior Publication Data

US 2002/0188917 A1 Dec. 12, 2002

(30) Foreign Application Priority Data

Jun. 8, 2001 (JP) ........................................ 2001-174075
Jun. 8, 2001 (JP) ........................................ 2001-174233

(51) Int. Cl.$^7$ .............................................. G06F 17/50
(52) U.S. Cl. .................... 716/4; 716/19; 716/1
(58) Field of Search ............................ 716/4, 19, 1, 20, 716/21

(56) References Cited

U.S. PATENT DOCUMENTS

| | | | | |
|---|---|---|---|---|
| 4,330,775 A | * | 5/1982 | Iwamoto et al. ............ | 382/141 |
| 4,958,373 A | * | 9/1990 | Usami et al. ............... | 382/149 |
| 5,764,363 A | * | 6/1998 | Ooki et al. .................. | 356/364 |
| 5,808,735 A | * | 9/1998 | Lee et al. ................. | 356/237.2 |
| 6,148,097 A | * | 11/2000 | Nakayama et al. ......... | 382/141 |
| 6,566,885 B1 | * | 5/2003 | Pinto et al. ................. | 324/501 |
| 6,578,188 B1 | * | 6/2003 | Pang et al. ................... | 716/19 |
| 2002/0114506 A1 | * | 8/2002 | Hiroi et al. ................. | 382/149 |

FOREIGN PATENT DOCUMENTS

| | | |
|---|---|---|
| JP | 60-031171 | 2/1985 |
| JP | 62-078659 | 3/1987 |
| JP | 01-149950 | 6/1989 |
| JP | 03-078749 | 4/1991 |
| JP | 07-078758 | 4/1995 |
| JP | 11-146983 | 5/1999 |
| JP | 11-178464 | 6/1999 |

* cited by examiner

Primary Examiner—Vuthe Siek
Assistant Examiner—Sun James Lin
(74) Attorney, Agent, or Firm—Lorusso, Loud & Kelly (57) ABSTRACT

A defect inspection method and a defect inspection apparatus accurately determine whether potential defects on a surface of a wafer are true defects, and restrains the oversight or the like of defects, permitting reliable quality assurance and accurate quality control to be achieved. The number and positions of detected potential defects are used as the parameters for determining whether potential defects are true defects. The density of potential defects is determined, and the determined density is compared with a set value to decide whether the potential defects are true defects. A surface of a wafer is captured using a differential interference microscope, and the image is processed to count the number of potential defects observed on the surface. The potential defects are detected at the spots where luminance shifts in the captured image. A spatial filter is applied to the captured image to enhance the area where the luminance shifts, and the enhanced area is binarized. This allows even adjoining potential defects to be detected without overlapping. Based on the characteristic amounts of the detected areas, it is decided whether the potential defects are true defects or noises, then the number of the true defects is counted.

14 Claims, 9 Drawing Sheets

CONSTRUCTION OF DEFECT INSPECTION APPARATUS

Fig.1

CONSTRUCTION OF DEFECT INSPECTION APPARATUS

Fig.2

DEFECT DETECTION EXAMPLE 1
DETECTED POTENTIAL DEFECTS

DEFECT DETECTION RESULT OBTAINED
BY CONVENTIONAL METHOD

Fig.4

DEFECT DETECTION EXAMPLE 1
DETECTED GRAVITY CENTERS

Fig.5

DEFECT DETECTION EXAMPLE 2
DETECTED DEFECTS

Fig.6

DEFECT DETECTION EXAMPLE 2
DETECTED GRAVITY CENTERS

Fig.7

ORIENTATION FLAT
OR NOTCH

DETERMINATION OF DEFECTS BASED ON INSPECTION RESULTS
OBTAINED AT POSITIONS SYMMETRICAL WITH RESPECT TO ORIGIN

Fig.8

CONSTRUCTION OF SYSTEM

Fig.9

ENHANCED AREA WHEREIN LUMINANCE CHANGES FROM BRIGHT TO DARK (CONCAVE OF DEFECT)

EXAMPLE OF DEFECT DETECTION RESULT OBTAINED
BY METHOD ACCORDING TO THE INVENTION

Fig.10

| 1 | 1 | 0 | -1 | -1 |
|---|---|---|----|----|
| 1 | 1 | 0 | -1 | -1 |
| 1 | 1 | 0 | -1 | -1 |

EXAMPLE OF SPATIAL FILTER 5 × 3

1 PIXEL OF CAPTURED IMAGE   R(a, b)
1 PIXEL OF SPATIAL FILTER        F(i, j)

WHEN FILTER SIZE IS n×m FOR PIXEL R (a, b), LUMINANCE
VALUE V (a, b) IS CALCULATED ACCORDING TO THE FOLLOWING
EXPRESSION:

$$V(a,b) = \sum_{j=1}^{m} \sum_{i=1}^{n} R(a-(n-1)/2+(i-1),\ b-(m-1)/2+(j-1))*F(i,\ j)$$

WHERE IF $V(a,b) > 255$, THEN $V(a,b)=255$
$V(a,b) < 0$, THEN $V(a,b)=0$

EXAMPLE OF FILTER FOR ENHANCING BOUNDARY

Fig.11B    Fig.11C    Fig.11D

THREE POTENTIAL DEFECTS

Fig.11E    Fig.11F    Fig.11G

ONE POTENTIAL DEFECT

EXAMPLES OF DEFECT DETECTION RESULTS OBTAINED BY
METHOD ACCORDING TO THE INVENTION

Fig.12

PROCESSING FLOWCHART

Fig.13

DEFECT INSPECTION METHOD AND DEFECT INSPECTION APPARATUS

BACKGROUND OF THE INVENTION

1. Field of the Invention

The present invention relates to a defect inspection method and a defect inspection apparatus for inspecting defects in an object to be inspected, such as a silicon wafer.

2. Description of the Related Art

Crystal defects of a silicon wafer or the like include oxidation induced stacking faults (OSFs) and bulk microdefects (BMDs). When a silicon wafer is etched, etch pits of a few $\mu$m depth may appear in the surface thereof. Etch pits exhibiting regularity corresponding to a face-centered tetragonal structure of a silicon wafer are referred to as the OSFs, while etch pits having irregular shapes are referred to as BMDs of oxidation deposits, microdisplacement, and stacking faults. Usually, the inspection for the OSFs or BMDs is visually performed with the aid of a microscope. The defects are visually checked and the number of such defects in an inspection visual field is counted to implement quality assurance and quality control of wafers on the basis of the counting result.

There has also been proposed methods whereby to capture microscopic images and process the images so as to detect and count defects. Examples of such methods are found in Japanese Unexamined Patent Application Publication No. 61-194737 entitled "SILICON WAFER OSF DENSITY INSPECTION METHOD" and Japanese Examined Patent Application Publication No. 6-71038 entitled "CRYSTAL DEFECT RECOGNIZING METHOD."

Here, according to a first defect inspection method, potential defects that have been processed into binarized images on the basis of the shape characteristics of defects are checked to determine whether they are truly defects. For instance, according to the method disclosed in Japanese Unexamined Patent Application Publication No. 61-194737, potential defects are checked against a reference shape to determine whether the candidates are truly defects. The method according to Japanese Examined Patent Application Publication No. 6-71038 involves the length and aspect ratio of a defect. These inspection methods focus only on the shapes of defects to make decisions. More specifically, only a reference shape or the shape of a defect involving the length or aspect ratio of the defect are used as determining parameters to decide whether the defect is a true defect.

According to a second defect inspection method, a predetermined threshold value is set for a captured image to binarize the image thereby to detect potential defects and to determine whether they are true defects on the basis of the characteristic amounts of the potential defects. Then, the quantity of the true defects is counted.

The first inspection method, however, presents the following problem since it uses only the shape of a potential defect as the determining parameter.

Figure 2:
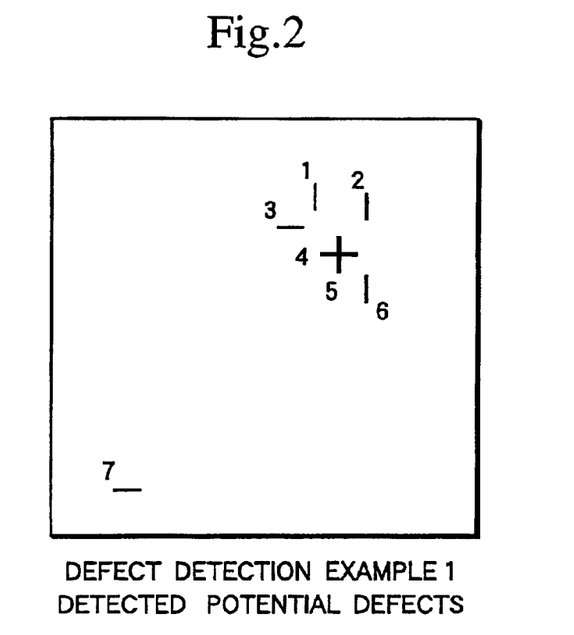
FIG. 2 is a schematic diagram of an example showing potential defects detected by the defect inspection apparatus according to the first embodiment of the present invention.

In the case of the potential defects shown in FIG. 2, judging from the shapes thereof, they may be determined to be OSFs, while it still remains uncertain from the aspect of their distribution of occurrence. More specifically, of the seven potential defects found in the visual field, six are very closely located. Such potential defects are normally produced from accidental contact of tweezers or some other foreign matters to the surface of a wafer during a process of etching a silicon wafer, and therefore, are not true defects that occurred on the surface of the wafer.

The conventional inspection method, however, makes it impossible to accurately discriminate the potential defects caused by tweezers coming in contact with the surface of a wafer. As a result, it is determined that there is a greater number of defects than there really is, thus interfering with accurate quality control.

The second inspection method presents the following problem.

The number of defects in an area measuring a few hundreds of $\mu$m squares per visual field is counted, meaning that the inspection of the whole surface of a wafer involves a few hundreds or tens of thousands of visual fields to be inspected. In the case of visual inspection, at least about one second is required to inspect one visual field, so that inspecting all visual fields takes too much time. Furthermore, human factors, such as the degree of fatigue of an inspector, inevitably lead to inconsistency in inspection results.

Figure 3A:
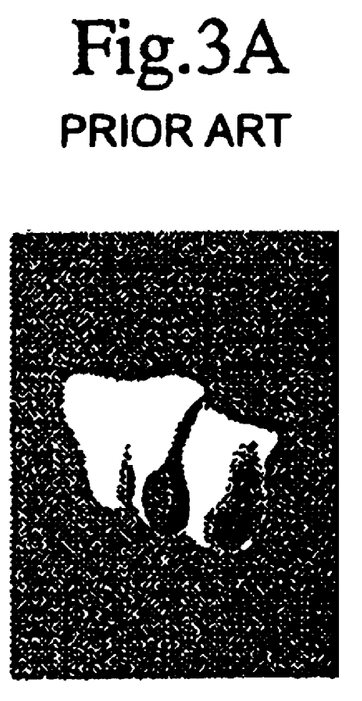
FIG. 3 is a schematic diagram showing defect detection results obtained by a conventional method.
Figure 3B:
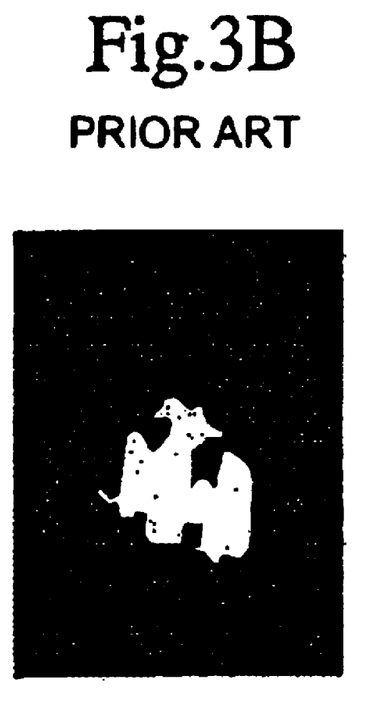

Although the method in which microscopic images are processed to count the number of potential defects solves the problem in the above visual inspection, the method presents the problem described below. Since captured images are simply processed into binarized images to detect defects, if there are many defects in an inspection visual field, as shown in FIG. 3A, it may happen that a plurality of closely located defects candidates shown in FIG. 3B are overlapped and misjudged to be a single defect. Especially in the case of BMDs, numerous defects frequently take place, so that the defects may be overlapped and detected as a single defect, thus posing a problem in achieving reliable quality assurance and quality control.

In addition, if a standard microscope is used, a captured defect of a few $\mu$m depth may be overlooked due to poor contrast, presenting another problem in achieving reliable quality assurance and quality control.

SUMMARY OF THE INVENTION

Accordingly, the present invention has been made with a view toward solving the problems discussed above, and it is an object of the present invention to provide a defect inspection method and a defect inspection apparatus that improve determination accuracy by using the distribution of detected defects as a parameter for determining whether a potential defect is a true defect, and also improve defect detection accuracy by preventing human errors and by accurately identifying micro-defects and closely located defects.

To this end, according to one aspect of the present invention, there is provided a defect inspection method for inspecting potential defects observed on a surface of an object to be inspected, wherein the number and the positions of the detected potential defects are used as determining parameters for determining whether the potential defects are true defects.

With this arrangement, the number of detected potential defects and the locations of the detected potential defects are used as the parameters for determining whether the potential defects are true defects, making it easier to recognize the potential defects (not true defects) that occurred due to contact of a foreign object, including tweezers, with a surface of an object to be inspected, such as a silicon wafer. The contact by a foreign object, such as tweezers, causes potential defects to take place closely located. More specifically, such potential defects may densely occur around a point or along a line. Therefore, it is possible to determine whether detected potential defects are true defects by measuring the density of the potential defects based on the number of detected potential defects and also the positions thereof.

Preferably, the density of potential defects is determined on the basis of the aforesaid number of potential defects and the positions thereof, and the determined density is compared with a preset value so as to decide whether the potential defects are true defects.

With this arrangement, if the determined density of potential defects based on the number of potential defects and the positions thereof exceeds the preset value, then it is determined that the potential defects are not true defects.

According to another aspect of the present invention, there is provided a defect inspection method wherein, to inspect potential defects observed on a surface of an object to be inspected, if a total number of potential defects in an inspection visual field is smaller than a preset value, then an area that is smaller than the inspection visual field is set, the gravity center position of a detected potential defect is aligned with the central position of the foregoing area, the number of potential defects in the area is counted, the density of the potential defects is determined on the basis of the ratio of the counted number of potential defects to the total number of potential defects in the inspection visual field, and it is decided whether the determined density of the potential defects exceeds a preset percentage so as to determine whether the potential defects are true defects.

With the arrangement discussed above, it can be determined that the density is higher as there are more potential defects in the area set to be smaller than the inspection visual field. On the other hand, the defects caused by the contact of a foreign object, such as tweezers, to a surface of an object to be inspected also lead to a higher density. For this reason, if statistical numerical data on the densities of defects resulting from generally assumed foreign objects is obtained by sampling or the like in advance, and the percentages against the whole inspection visual field are preset, then comparison with the preset percentages makes it possible to easily determine whether potential defects are true defects. In other words, if the densities are higher than the preset percentages, then it is determined that the potential defects are not true defects.

According to still another aspect of the present invention, there is provided a defect inspection method wherein, to inspect potential defects observed on a surface of an object to be inspected, if a total number of potential defects in an inspection visual field is smaller than a preset value, then the gravity center positions of all potential defects are determined, an n-order approximate curve is determined on the basis of the distribution of the gravity center positions, the number of potential defects existing in a set width along n-order approximate curve is counted, the density of the potential defects is determined on the basis of the ratio of the counted number of the potential defects to the total number of potential defects in the inspection visual field, and it is determined whether the density of the potential defects is a preset ratio or more so as to determine whether the potential defects are true defects.

In the configuration described above, a foreign matter, such as tweezers, may point-contact or line-contact with a surface of an object to be inspected, such as a silicon wafer. In the case of the line contact, the distribution of the gravity center positions of potential defects will be linear. Hence, an n-order approximate curve is drawn along the distributed gravity center positions of the potential defects. If the density of potential defects along the n-order approximate curve is high, then it is determined that the potential defects are not true defects.

According to yet another aspect of the present invention, there is provided a defect inspection method wherein, to inspect potential defects observed on a surface of an object to be inspected, if a total number of potential defects in an inspection visual field is smaller than a preset value, then the gravity center positions of all potential defects are determined, and the distances among the potential defects are calculated on the basis of the gravity center positions to determine the mean value of the distances. Then, it is determined whether the distance that is smaller than the value obtained by adding or subtracting an offset value preset for the determined mean value is a preset ratio or more against the number of combinations of the distances among all potential defects in the inspection visual field so as to determine whether the potential defects are true defects.

This arrangement makes it possible to determine the density of potential defects and to determine whether the potential defects are true defects on the basis of the determined density, as in the case of the aspects of the present invention discussed above.

In a preferred form of the present invention, if it is determined that observed potential defects are not true defects, then inspection is carried out in a visual field in the vicinity of the inspected visual field.

With the arrangement discussed above, in the case of potential defects caused by contact of a foreign object or the like, then the visual field adjacent to an inspected visual field is inspected to determine the condition of a true defect. In this case, a concentric adjoining visual field is most likely to be inspected.

In a preferred form of the present invention, the inspection results at two positions that are symmetrical on the whole surface of an inspected object are compared, and it is determined whether the difference therebetween exceeds a preset value so as to determine whether potential defects are true defects.

In the above arrangement, at the two symmetrical positions, the numbers of true defects are considered to be substantially the same, due to the CZ method. According to the CZ method, an ingot is drawn up while rotating it. At this time, crystal growth simultaneously occurs on a concentric circle, usually producing the same state. Hence, if defects occur, then the defects tend to be concentrically distributed. This means that whether potential defects are true defects can be determined by comparing the states of potential defects at a plurality of concentric spots. More specifically, the inspection results at two symmetrical positions are compared, and if the difference therebetween exceeds a preset value, then the potential defects are considered to be attributable to some external cause and it can be determined that they are not true defects.

According to a further aspect of the present invention, there is provided a defect inspection method wherein a surface of an object to be inspected is captured using a differential interference microscope, the obtained image is processed to count the number of potential defects observed on the surface, and potential defects are detected at the spots where luminance is different in the captured image.

With the arrangement described above, an image captured using the differential interference microscope shows defective spots exhibiting irregularities compared with the rest of a surface, and the luminance therefore is different at the defective spots in the captured image. Thus, it may be determined that the spot having a difference luminance has a potential defect, and the spot is checked for a true defect.

In a preferred form of the present invention, a spatial filter is applied to the captured image to enhance the spot exhibiting the different luminance, and the enhanced spot is subjected to a binarizing process to detect a potential defect. Based on the characteristic amount of the detected spot, it is determined whether the potential defects are true defects or noises, then the number of true defects is counted.

This arrangement enables potential defects to be reliably recognized by applying the spatial filter to enhance spots where luminance changes. Moreover, a plurality of adjoining potential defects can be also clearly identified as separate individual potential defects. Binarizing the spots that have been enhanced by the spatial filter clarifies potential defects, permitting easier detection. Then, based on the characteristic amounts of the detected spots, it is determined whether the potential defects are true defects or noises, thus allowing the number of only true defects to be counted.

According to a further aspect of the present invention, there is provided an inspection apparatus adapted to capture a surface of an object to be inspected by a differential interference microscope and to carry out image processing to count the number of potential defects observed on the surface, the inspection apparatus being equipped with a defect detecting unit for detecting potential defects at spots exhibiting different luminance in the captured image.

With the arrangement, the differential interference microscope displays the irregularities of captured defective spots in terms of different luminance, and the defect detecting unit detects potential defects at the spots having the different luminances in the captured image.

Preferably, the defect inspection apparatus is equipped with a boundary enhancing unit that applies a spatial filter to the captured image to enhance a boundary area where luminance changes, and processes the boundary area into a binary-coded image to obtain a clear potential defect image, a defect detecting unit for detecting the potential defects that have been enhanced and clarified by the boundary enhancing unit, and a defect counting unit that determines whether the potential defects are true defects or noises on the basis of the characteristic amount of the area detected by the defect detecting unit, then counts the number of true defects.

With this arrangement, the boundary enhancing unit enhances a boundary area by using a spatial filter to clarify the presence of potential defects. Even if a plurality of adjoining potential defects is present, each of the potential defects can be clearly identified and recognized. The defect detecting unit binarizes the area enhanced by the spatial filter of the boundary enhancing unit so as to clarify and detect potential defects. Then, based on the characteristic amount of the detected area, the defect counting unit determines whether the detected potential defects are true defects or noises, and counts the number of only true defects.

DESCRIPTION OF THE PREFERRED EMBODIMENTS

The embodiments in accordance with the present invention will now be described in conjunction with the accompanying drawings.

First Embodiment

In this embodiment, the descriptions will be given of a defect inspection apparatus and three different defect inspection methods.

Defect Inspection Apparatus

Figure 1:
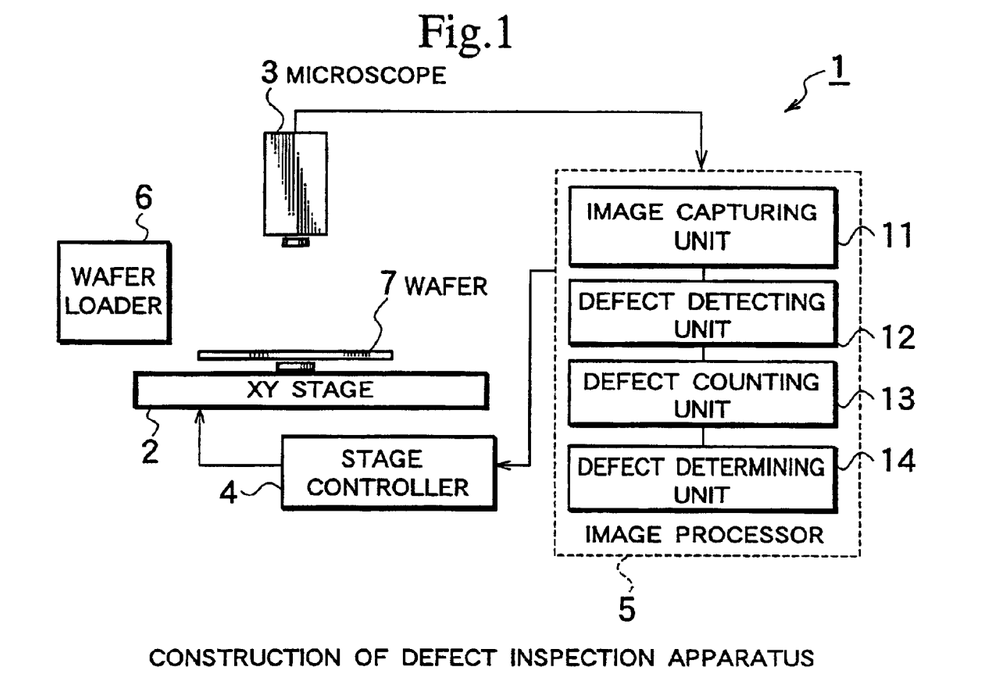
FIG. 1 is a block diagram showing a schematic construction of a defect inspection apparatus according to a first embodiment of the present invention.

FIG. 1 shows the construction of a silicon wafer defect inspection apparatus 1 in accordance with the first embodiment. In this embodiment, an OSF inspection will be explained.

As shown in the drawing, the defect inspection apparatus 1 is constructed of an XY stage 2, a microscope 3, a stage controller 4, an image processor 5, and a wafer loader 6.

The XY stage 2 supports and accurately moves a wafer 7 rested thereon in XY directions to adjust to the position of the microscope 3. The XY stage 2 is also capable of moving up or down or rotating the wafer 7, as necessary.

The microscope 3 used to observe the surface of the wafer 7 converts the image of the surface of the wafer 7 that has been captured by a CCD camera or the like into electric signals and transmits the electric signals to the image processor 5. The microscope 3 may be of any type as long as it is capable of detecting micro defects on the surface of the wafer 7 in the form of images. Normally, a differential interference microscope is used; however, various other types of microscopes, such as an optical microscope with bright visual field, capable of detecting defects may alternatively be used.

The stage controller 4 controls the XY stage 2 to adjust the surface of the wafer 7 to be inspected to the visual field of the microscope 3.

The image processor 5 captures and processes an image of the surface of the wafer 7 to be inspected. The image processor 5 is connected to the XY stage 2 and the microscope 3 to control the XY stage 2 through the intermediary of the stage controller 4 so as to move the surface of the wafer 7 to be inspected to right under the microscope 3. The image from the microscope 3 is captured in the form of electric signals into the image processor 5.

To be more specific, the image processor 5 is constituted by an image capturing unit 11, a defect detecting unit 12, a defect counting unit 13, and a defect determining unit 14. The image capturing unit 11 processes an image of an inspection visual field captured from the microscope 3. More specifically, the image capturing unit 11 carries out processing, such as binarizing the captured image by using a predetermined luminance threshold value to display potential defects in the form of clear images. The defect detecting unit 12 detects potential defects from the image of the inspection visual field. The defect counting unit 13 counts the number of potential defects according to the devices that will be discussed hereinafter. The defect determining unit 14 determines whether the detected potential defects are true defects according to the devices that will be discussed hereinafter.

The wafer loader 6 carries the wafer 7 to be inspected and sets it on the XY stage 2, and also carries the wafer 7 to the next step or the like after completion of the inspection.

First Defect Inspection Method

A first defect inspection method for silicon wafers that uses the foregoing defect inspection apparatus 1 will now be explained.

First, the wafer 7 is set at a predetermined position on the XY stage 2 by the wafer loader 6. Then, the wafer 7 set on the XY stage 2, which is controlled by the stage controller 4, is moved to the position where the object is to be inspected, and the surface of the wafer 7 is observed by the microscope 3. The image captured by the microscope 3 is processed by the image processor 5. In the image processor 5, the image capturing unit 11 carries out processing, such as binarization, to display clear images of potential defects from the image of an inspection visual field captured by the microscope 3.

Figure 4:
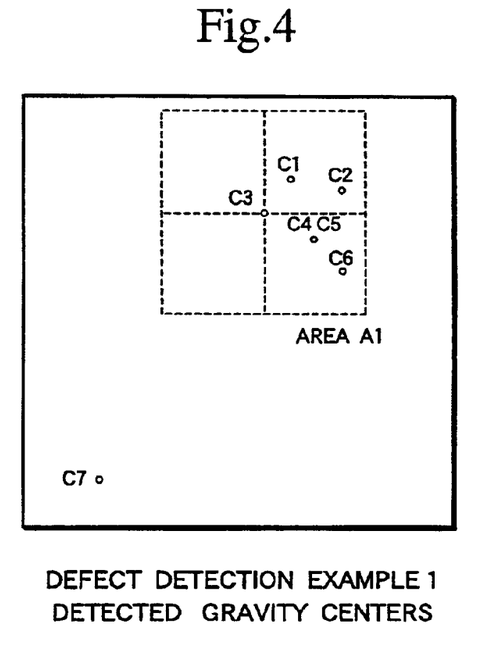
FIG. 4 is a schematic diagram showing an example in which gravity centers have been detected from potential defects shown in FIG. 2.

Subsequently, the defect detecting unit 12 quantitatively detects potential defect areas from the inspection visual field, and the defect counting unit 13 counts the number of potential defects. In this case, it is assumed that the image shown in FIG. 2 has been taken. The image shown in FIG. 2 is an example illustrating potential defects that occurred due to tweezers contacting the surface of the wafer when handling the wafer during an etching process. Gravity center Ci ("i" denotes the label number of a potential defect; i=7 in this case) of a potential defect is determined from the image of each potential defect shown in FIG. 2. FIG. 4 shows an image showing the gravity centers Ci of the individual potential defects.

The defect determining unit 14 determines the density of the potential defects on the basis of the distribution of the potential defects in the image shown in FIG. 4. First, as shown in FIG. 4, an area A1, which is smaller than the inspection visual field, is set, the central position coordinate of the area A1 is aligned with the gravity center of a potential defect, and a number AK of the potential defects in the area A1 is counted. In this case, if the central position coordinate of the area A1 is aligned with a potential defect gravity center C3, then six potential defects are found. The number AK is counted on other potential defects in the same fashion. A maximum value among the numbers of potential defects AK determined as described above provides the evaluation criterion. In this case, AK=6.

The defect determining unit 14 applies this method when a total number of potential defects n1 within the inspection visual field ranges from 3 to 30, a ratio R1 of the number of potential defects AK in the area A1 to a total number of potential defects n1 in the inspection visual field is 70% or more. If R1=70% or more, then it is determined that the potential defects are not true defects. Reasonable values based on statistics of actual measurements are used for these preset values.

According to the standard, 70% of the total number, 7, of potential defects in the inspection visual field is 5 (decimal places being rounded off), while the number of potential defects AK in the area A1 is 6. Hence, it is determined that the potential defects are not true defects.

Thus, if it is determined that the potential defects are not true defects, then the inspection visual field is shifted to repeat the inspection explained above. In this case, the inspection is performed on the visual field adjacent to the one that has been inspected. More specifically, the XY stage 2 is moved by 1000 $\mu$m in an X-axis direction, or by 1000 $\mu$m in a Y-axis direction to inspect the visual field that has not yet been inspected. In this case, the inspection is carried out mostly on a concentric adjacent visual field because of the characteristics of the CZ method described above. Potential defects caused by the contact or the like of a foreign object are considered to be present only in the inspected visual field; therefore, the visual field adjacent thereto is inspected to check the states of true defects.

Based on the inspection results obtained from the determination discussed above, final determination of defects is carried out.

Figure 5:
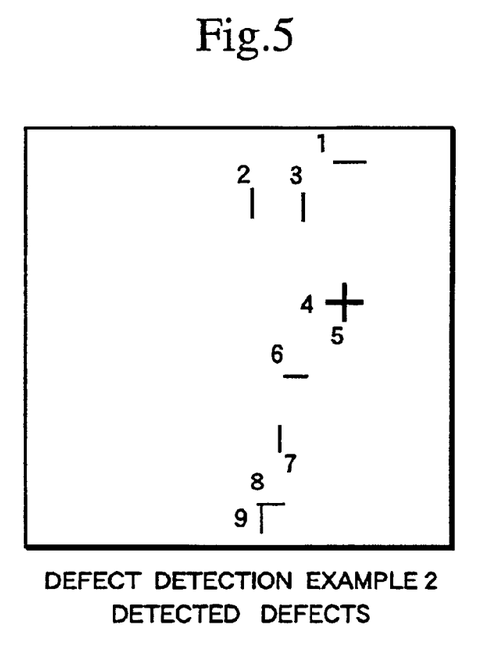
FIG. 5 is a schematic diagram showing another example in which potential defects have been detected by the defect inspection apparatus according to the first embodiment of the present invention.

In the case of the wafer 7, the states at the positions symmetrical with respect to an origin are considered substantially the same because of the handling method thereof. More specifically, if the potential defects as shown in FIG. 2 and FIG. 5 are found on one side, then similar potential defects are very likely to exist on the other side symmetrical with respect to the origin.

Figure 7:
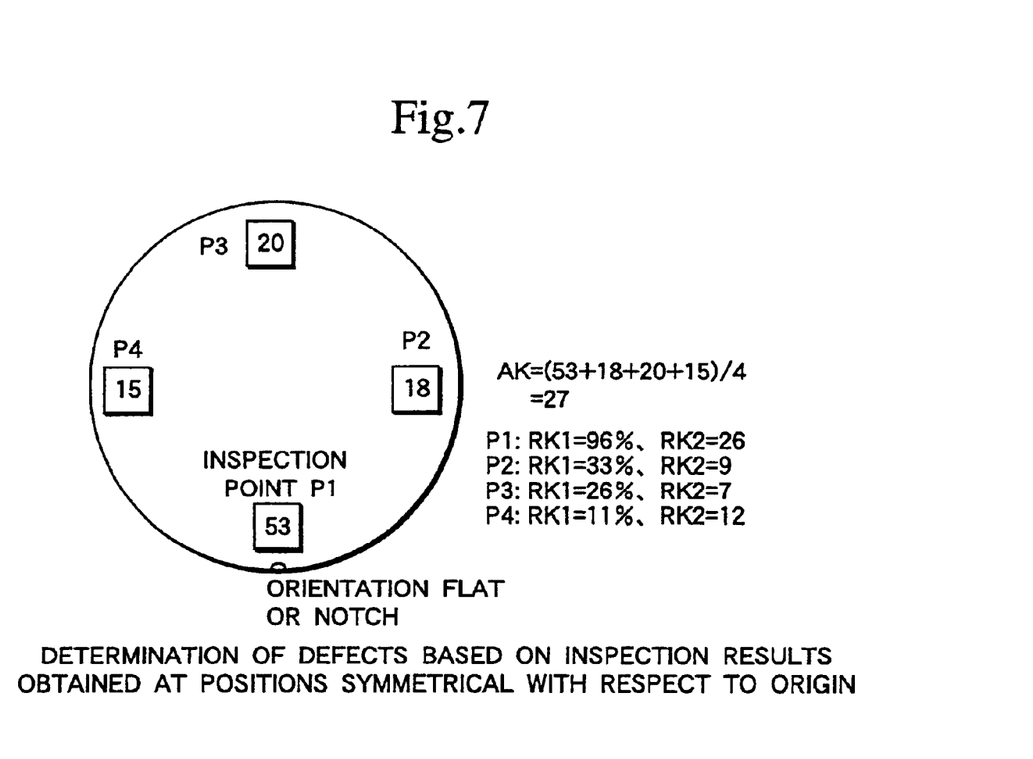
FIG. 7 is a plan view showing a wafer that indicates the positions where final determination of defects is carried out.

Accordingly, as shown in FIG. 7, the inspection results obtained at two positions that are symmetrical with respect to the origin on the entire surface of the inspected wafer 7 are compared, and it is decided whether the difference between the inspection results exceeds a preset value so as to decide whether the potential defects are true defects.

In this case, one inspection result is denoted as K1, while the other inspection result is denoted as Ki (i=2,3, and so on). K1 and Ki indicate the results obtained at inspection points corresponding to the positions symmetrical with respect to the origin (in the vicinity of both ends in the radial direction of the wafer 7) and in the vicinity thereof.

RK1 and RK2 are calculated according to the expressions shown below, using the mean value of the total number of potential defects of Ki at this time denoted as AVK:

$$RK1=(|Ki-AVK|/AVK) \times 100(\%)$$

$$RK2=|Ki-AVK|$$

If the following conditions are satisfied, then it is determined that the potential defects include those that are not true defects:

$$RK1 > JP1 \text{ (where } JP1=50\%)$$

$$RK2 > JP2 \text{ (where } JP2=20)$$

RK1 denotes the ratio of a difference with respect to the mean value at an inspection point i. RK2 denotes the deviation from the mean value at the inspection point i. JP1 and JP2 are the threshold values for determining whether potential defects are true defects. The threshold values JP1 and JP2 are set beforehand in a table for the numbers of potential defects found in one visual field. Regarding JP1, if an inspection result shows a deviation of 50% or more from a mean value, then it is determined that the potential defect is not a true defect. Regarding JP2, if the difference is 20 or more, then it is determined that a potential defect is not a true defect.

Thus, it is determined that point P1 shown in FIG. 7 is not a true defect. As described above, according to the CZ method, true defects are similarly distributed on concentric circles; therefore, all the four points should exhibit the same values if they are true defects. However, only inspection point P1 satisfies the above conditions, so that it is determined that the inspection point P1 has been caused by contact or the like of tweezers rather than being a true defect.

Although the mean values have been used for the determination in this case, any of defect measurements Ki may alternatively be used as the reference.

After the inspection is completed as described above, it is determined whether a visual field wherein a potential defect detected by the inspection performed as described above has been judged to be a non-true defect exists, and the determination result is recorded as an inspection result. For instance, the wafer 7 may be directly marked, the image stored during the inspection may be marked, or a record may be added into a result file for future reference by an inspector.

In this case, the inspection images are saved, so that the inspection image is framed with red. This enables an inspector to easily recognize the inspection image with the red frame later to perform proper inspection, processing, etc. in the future.

Second Defect Inspection Method

If an image as shown in FIG. 5 is obtained, then the defect determining unit 14 makes a decision on the basis of an n-order approximate curve.

Figure 6:
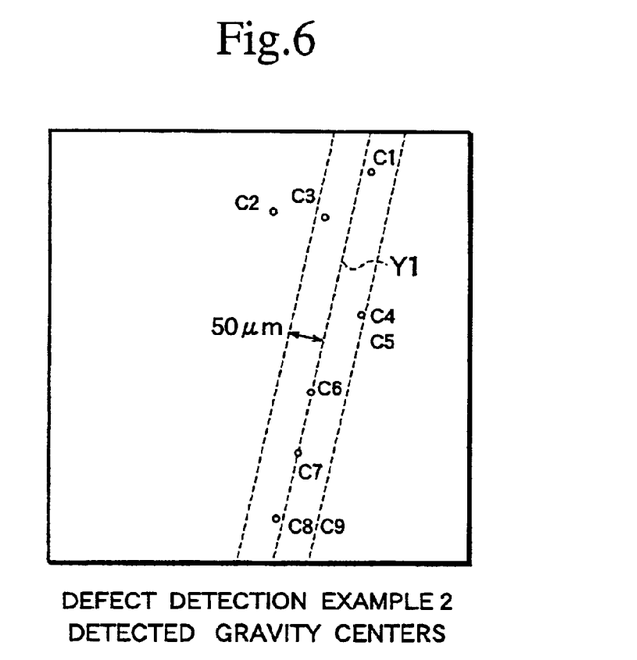
FIG. 6 is a schematic diagram showing an example in which gravity centers have been detected from potential defects shown in FIG. 5.

First, in the same manner as that of the first defect inspection method discussed above, the gravity centers Ci (i=9) of potential defects are determined, as shown in FIG. 6. Based on the distribution of the gravity centers Ci, the n-order approximate curve is determined, first function being applied in this case. More specifically, a straight line Y1 is obtained as the approximate line with respect to the distribution of Ci. The approximate straight line Y1 indicates the line generated by tweezers or the like coming in contact with the surface of the wafer 7 and being dragged.

A predetermined width W1 is set for the approximate straight line Y1, and the number of potential defects AK in the range defined by the width W1 is counted. In this case, as shown in FIG. 6, the width perpendicular to the approximate straight line Y1 was set to 50 μm, and the number of potential defects AK in the range defined by the width was counted. The result showed 8.

The determination is carried out under the following conditions: the total number of potential defects n1=5 to 30, and the ratio R1 of the number of potential defects AK to the total number of potential defects n1 is 70%. Reasonable values are preset for W1, n1, and R1 on the basis of the statistics of actual measurements.

Seventy percent of the total number, nine, of potential defects is six, while the number of potential defects AK within the predetermined width W1 of the approximate straight line Y1 is eight. Hence, it is determined that the potential defects are not true defects.

Thereafter, final determination of defects is implemented in the same manner as that in the foregoing defect inspection method, and the inspection result is recorded on the wafer 7, etc.

Third Defect Inspection Method

This method represents an example in which the defect determining unit 14 determines whether potential defects are true defects on the basis of the distance between potential defects calculated from the positions of the individual potential defects.

First, gravity centers Ci of potential defects are determined, as shown in FIG. 4, in the same manner as in the first defect inspection method described above. Based on the gravity center positions, a distance Lij between the potential defects is calculated. The distance Lij represents the distance from the gravity center Ci of a potential defect to a gravity center Cj of another potential defect. For instance, L12 denotes the distance from a gravity center C1 to a gravity center C2.

In this case, there are seven potential defects; hence, i=1 to 7, j=2 to 7, j>i, and the distance Lij is calculated on the basis of the coordinates of the gravity center Ci and the gravity center Cj according to the expression shown below.

When the gravity center Ci has an X-coordinate CXi and a Y-coordinate CYi, and the gravity center Cj has an X-coordinate CXj and a Y-coordinate CYj, the distance Lij is determined by:

$$Lij = \sqrt{((CXi-Cxj)^2 + (CYi-CYj)^2)}$$

A mean value AL is determined from the distances Lij (i=1 to 7, j=2 to 7, j>i) of all potential defects obtained by the above expression.

Then, a preset offset value α is added to or subtracted from the mean value AL to determine an evaluation criterion JAL.

$$JAL = AL + \alpha (\alpha = -50)$$

where JAL=β if JAL<β (β=300)

The offset values α and β have the meanings described below.

True defects are relatively evenly distributed in an inspection visual field. For this reason, the distance between potential defects widely ranges from top to bottom with a mean value thereof being at the middle. In contrast to this, the potential defects caused by an external factor, such as tweezers, tend to be concentrated at a particular portion in an inspection visual field. Hence, there are more distances between potential defects that are smaller than a mean value. If a majority of the potential defects in the inspection visual field are concentrated in one area, while a small number of potential defects are distributed over the entire visual field, then all the distances between the potential defects concentrated in one area will be significantly smaller than a mean value even if the mean value of the distances between the potential defects is large. Accordingly, if many combinations of potential defects exhibit values smaller than the value obtained by subtracting a predetermined value, namely, the offset value α, from the mean value, then it can be determined that the potential defects are concentrated in one area. This means that the potential defects are not true defects.

In this case, in a standard distribution of potential defects, which exhibits relatively even distribution, the mean value of the distances between potential defects when 50 potential defects are found per visual field will be one fifth of the mean value of the distances between potential defects when ten potential defects are detected per visual field. In other words, the mean value of the distances between potential defects when ten potential defects are detected is long, while the mean value of the distances between potential defects when 50 potential defects are detected is short. Hence, the offset value α is adjusted according to the magnitude of a mean value.

The lower limit of the evaluation criterion JAL is set by the value β. Usually, the distances can be known in terms of a rough value beforehand for a particular number of potential defects that take place, so that β is used accordingly. For example, if there are ten potential defects in one visual field such that the potential defects are concentrated in one area, that is, if they are not true defects, then the evaluation criterion JAL determined only on the basis of a mean value will be of a small value. As a result, the evaluation criterion JAL of the small value may cause non-true defects to be judged as true defects. To avoid this, a minimum value β of the evaluation criterion JAL is set on the basis of the number of potential defects in one visual field.

Thus, α and β take variables that change according to the number of potential defects existing in one visual field. Specific values for the variables will be reasonable values preset on the basis of the statistics of actual measurements.

In this case, there are seven potential defects, so that there are 21 combinations of the distances between potential defects. Actual measurement results revealed that the mean value of the detection results in FIG. 4 was AL=253. This value is smaller than the minimum value β=300 of the evaluation criterion JAL; hence, JAL=300.

Of the distances between potential defects, there were fifteen combinations exhibiting the evaluation criterion JAL=300 or less.

The ratio (determination standard) for the number of combinations of distances between all potential defects in the inspection visual field is set to R2=70% to carry out the determination.

There are 21 combinations of the distances between potential defects, so that 21×70%=15, while there are 15 combinations having the evaluation criterion JAL=300 or less. Accordingly, it is determined that the potential defects are not true defects.

Thereafter, final determination of defects is carried out in the same manner as in the first defect inspection method described above, and the inspection result is recorded on the wafer 7, etc.

Advantage

Thus, the methods described above permit accurate determination of whether the potential defects observed on the surface of the wafer 7 are true defects. This makes it possible to reduce the errors in counting defects, allowing more reliable quality assurance and more accurate quality control to be achieved.

Second Embodiment

A second embodiment in accordance with the present invention will now be explained.

The defect inspection method and the defect inspection apparatus according to this embodiment improve defect detection accuracy by using a differential interference microscope to obtain images with good contrast without overlooking defects of extremely small depths of a few μm. The differential interference microscope utilizing optical interference based on optical path differences is capable of detecting the depth differences of defects from a depth that is a few times the optical wavelength to about ¹⁄₁₀₀₀ of the optical wavelength as luminance differences. If, however, potential defects are close to each other, the images of the potential defects may overlap. For this reason, changes in luminance will be used in combination with luminance differences in the present invention. Luminance changes at an irregular portion, thus allowing even a plurality of adjoining potential defects to be clearly identified and detected as separate individual potential defects by detecting the changes in luminance. Furthermore, use of a spatial filter allows the boundary areas of potential defects to be enhanced. This makes it possible to avoid missing potential defects of a very small depth and to precisely identify a plurality of adjacent potential defects so as to permit detection of an accurate number of potential defects.

The following will describe this embodiment in conjunction with the accompanying drawings.

Defect Inspection Apparatus

Figure 8:
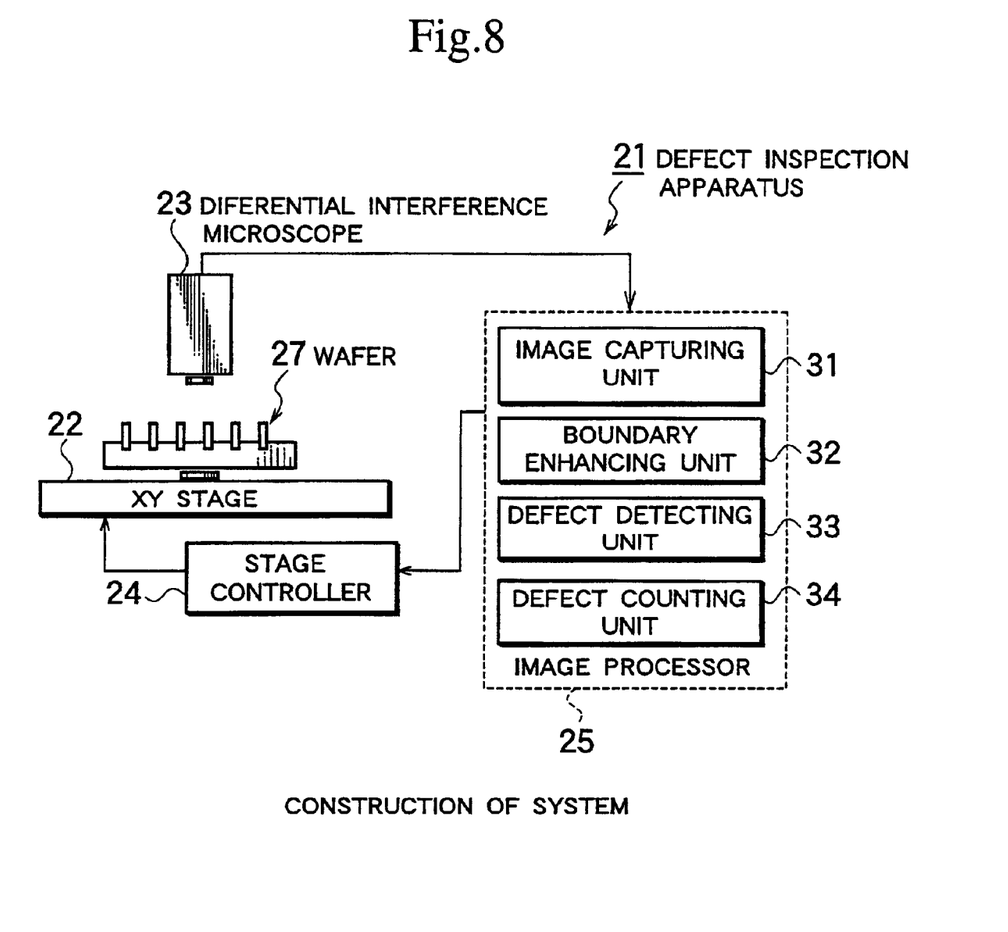
FIG. 8 is a block diagram showing a schematic construction of a defect inspection apparatus according to a second embodiment of the present invention.

FIG. 8 shows the construction of a defect inspection apparatus 21 for silicon wafers in accordance with the embodiment. In this embodiment, the descriptions will be given of the BMD inspection.

As shown in the drawing, the defect inspection apparatus 21 is constructed of an XY stage 22, a differential interference microscope 23, a stage controller 24, and an image processor 25.

The XY stage 22 supports and accurately moves a wafer 27 rested thereon in XY directions to the position of the differential interference microscope 23. The XY stage 22 is also capable of moving up or down or rotating the wafer 27, as necessary.

The differential interference microscope 23 used to observe a section of the wafer 27 converts the image of the section of the wafer 27 that has been captured by a CCD camera or the like into electric signals and transmits the electric signals to the image processor 25. The differential interference microscope 23 captures optical path difference of light in terms of interference, enabling the microscope 23 to detect an interference in the form of a level difference or a step as long as an interference takes place due to the presence of an optical path difference. Hence, the microscope 23 is capable of detecting a level difference of a potential defect of a few times the optical wavelength to about ¹⁄₁₀₀₀ of the optical wavelength.

Furthermore, in order to complement the detection based on a level difference, changes in luminance are used as a parameter for determination. Detecting only a level difference may not assure accurate identification of a plurality of adjacent potential defects. Detecting changes in luminance permits the detection of convexes and concaves, and the convexes and concaves are present in individual potential defects. This means that detection of convexes and concaves permit reliable detection of the presence of individual potential defects. Normally, a potential defect taking place on the wafer 27 has one concave. Since one potential defect has one concave, detecting a change in luminance makes it possible to identify each potential defect, allowing the number of potential defects to be detected. Thus, potential defects, which are micro irregularities existing on the surface of the wafer 27, can be accurately detected.

The stage controller 24 controls the XY stage 22 to bring the surface of the wafer 27 to be inspected to the visual field of the differential interference microscope 23.

The image processor 25 captures and processes an image of the surface of the wafer 27 to be inspected. The image processor 25 is connected to the XY stage 22 and the differential interference microscope 23 to control the XY stage 22 through the intermediary of the stage controller 24 so as to bring the surface of the wafer 27 to be inspected to right under the differential interference microscope 23. The image from the differential interference microscope 23 is captured in the form of electric signals into the image processor 25.

To be more specific, the image processor 25 is constituted by an image capturing unit 31, a boundary enhancing unit 32, a defect detecting unit 33, and a defect counting unit 34.

The image capturing unit 31 processes a captured image captured from the differential interference microscope 23, and sends the processed image to the boundary enhancing unit 32 for enhancing.

The boundary enhancing unit 32 carries out image processing of potential defects on the basis of spots where luminance changes in the captured image. The boundary enhancing unit 32 applies a spatial filter to the captured image to enhance the boundary areas where the luminance changes and also to binarize the areas to produce a clear potential defect image.

Figure 9:
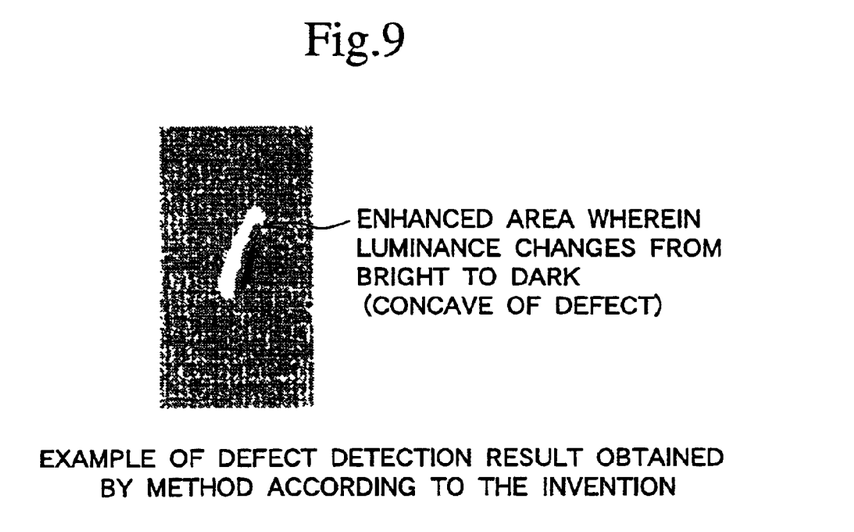
FIG. 9 is a schematic diagram showing one potential defect that has been found.

The luminance changes at the concaves of potential defects. Referring to FIG. 9, it can be seen that the luminance changes from the bright to the dark from the left to the right. In this case, the position at which the luminance changes can be adjusted by changing a shear amount. In this case, the shear amount has been adjusted so that the boundary of the bright and the dark is located at the center of the potential defect. Alternatively, the adjustment may be made so that the boundary is located at a different position, e.g., at an edge of the potential defect.

In the BMD, if there are multiple potential defects, as shown in FIG. 3A, then they may be observed in an overlapped state, as shown in FIG. 3B. This is for differentiating the entire image to remove variations in luminance and enhance the edges of the potential defects, then for binarizing the resulting image to perform detection. In this case, since the potential defect images are overlapped, they may be misjudged as a single potential defect, making it impossible to accurately detect the number of the potential defects.

Figure 10:
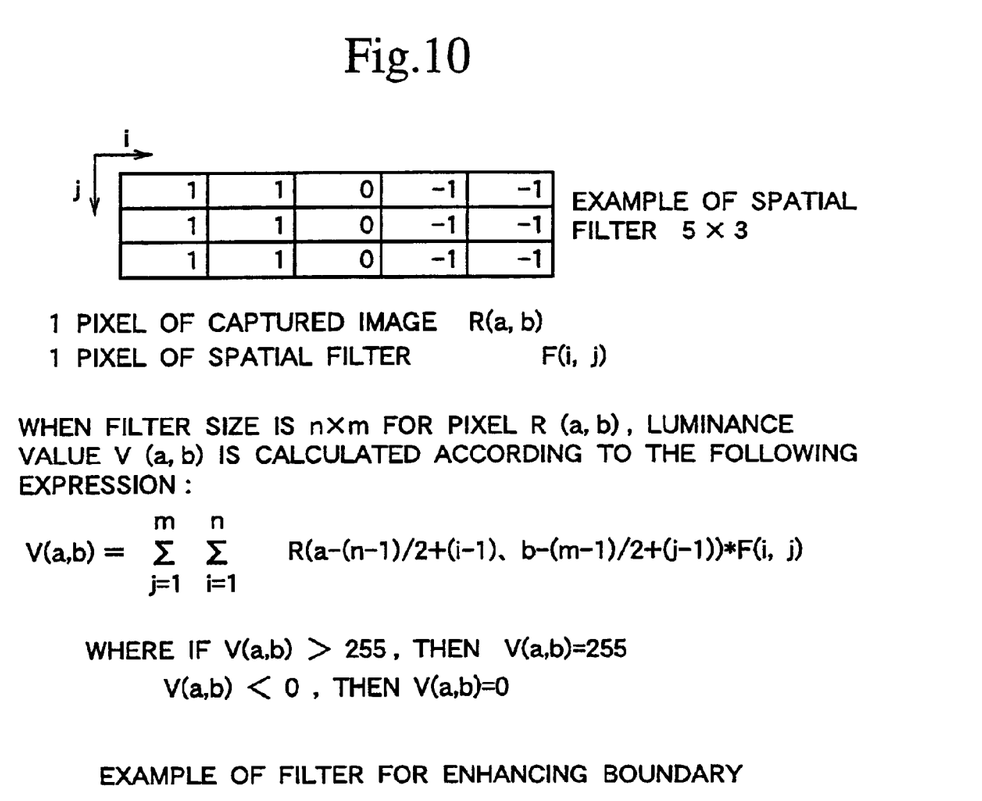
FIG. 10 is a diagram showing an example of a spatial filter.
Figure 11B:
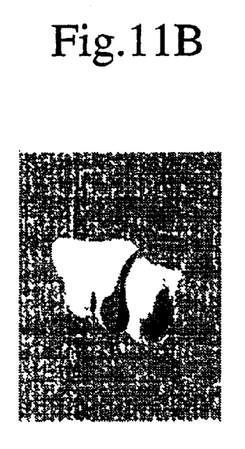
FIG. 11B schematically shows three potential defects that occurred, FIG. 11E schematically shows one potential defect that occurred, FIGS. 11C and 11F schematically show the potential defects that have been enhanced by applying the spatial filter, and FIGS. 11D and 11G schematically show the boundary-enhanced images that have been processed into binary-coded images.
Figure 11C:
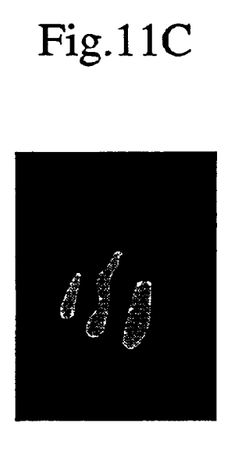
Figure 11D:
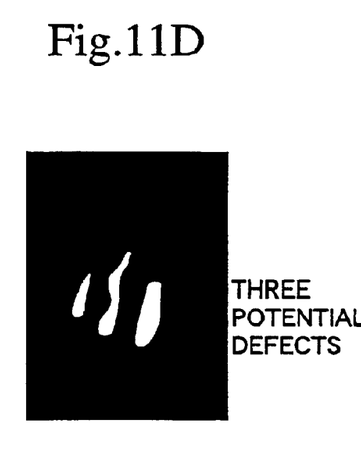
Figure 11E:
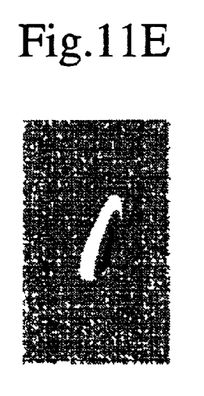
Figure 11F:
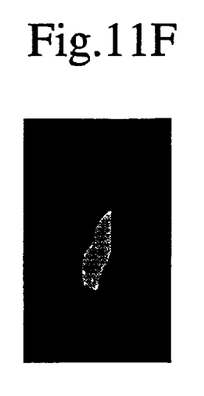
Figure 11G:
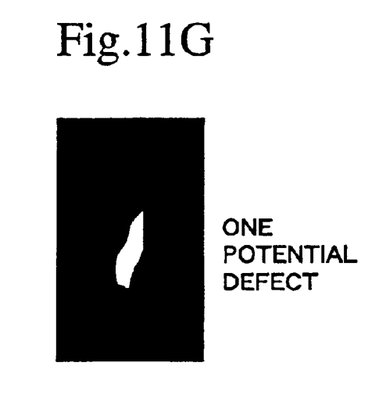

To avoid such a problem, the image captured by the differential interference microscope 23 is moved in one direction by the XY stage 22 to detect the boundary area where the luminance changes from the bright to the dark. This causes a single boundary area to be recognized as a single potential defect. According to the shapes of the potential defects on the wafer 27, one potential defect normally includes one boundary area of the bright and the dark observed as the image is moved. Therefore, one such boundary area that has been found can be considered to indicate the presence of one potential defect. This allows the multiple potential defects to be recognized as separate potential defects without the overlapping of the potential defect images. The boundary area of the bright and the dark is enhanced by applying a spatial filter. An example of the spatial filter is shown in FIG. 10. The processing implemented by the spatial filter turns the images shown in FIGS. 11B and 11E into the images shown in FIGS. 11C and 11F. The enhanced images are binarized using a predetermined threshold value to cause the potential defects to be displayed as the images of the potential defects with clear contrast, as shown in FIGS. 11D and 11G.

The defect detecting unit 33 carries out image processing, such as pattern recognition, to detect the potential defects that have been enhanced and clarified by the boundary enhancing unit 32. In this case, even when there are a plurality of adjoining potential defects, their images will not be overlapped, permitting accurate detection of the images of the potential defects to be achieved.

The defect counting unit 34 determines whether the potential defects detected by the defect detecting unit 33 are true defects or noises on the basis of the characteristic amounts thereof, then counts the true defects. The following information is used as the characteristic amounts. As the information regarding the shapes of potential defects, the areas equivalent to the numbers of pixels of detected potential defects, and the horizontal Fere diameters and the vertical Fere diameters representing the lengths of the sides of circumscribed rectangle of the potential defect are measured. In addition, as the information regarding the luminance of the potential defects, the average luminance, the maximum luminance, and the minimum luminance of the detected potential defects are mainly determined.

In this embodiment, it is determined whether the potential defects are true defects or noises on the basis of the characteristic amounts described above. The potential defects have already been enhanced by the filtering, and the images have been binarized to detect the potential defects. Hence, it is considered that most of the detected potential defects are considered to be true defects. Among the defects, those that were extremely small were difficult to clearly detect by visual inspection; therefore, it was decided to determine as a noise if an area A is smaller than a predetermined value THA, or as a true defect if the area A exceeds the predetermined value THA. In this embodiment, the processing is carried out, setting the threshold value as THA=3.

Defect Inspection Method

Figure 12:
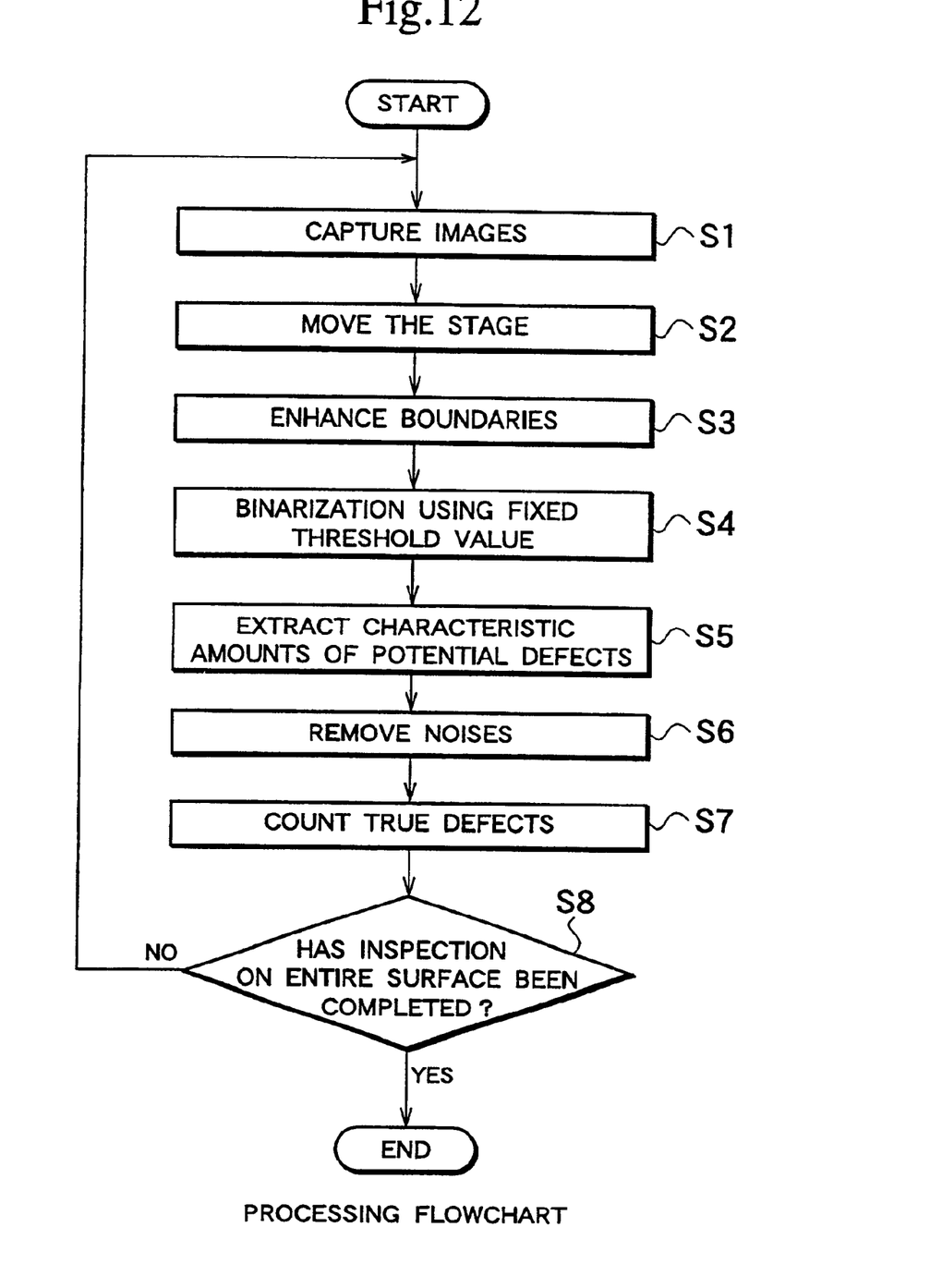
FIG. 12 is a flowchart illustrating the procedure of the inspection processing carried out by the defect inspection apparatus.

The defect inspection method for silicon wafers that uses the foregoing defect inspection apparatus 21 will now be explained in conjunction with the processing flow shown in FIG. 12.

A plurality of cleaved wafers 27 is set on a jig, and the jig is fixed at a predetermined position of the XY stage 22. In this embodiment, the jig is set such that the sections of the wafers are oriented in the vertical direction of the visual field to perform the inspection.

The wafers 27 are moved by the XY stage 22 controlled by the stage controller 24 to an inspection position, and the images of the sections of the wafers 27 are captured by the differential interference microscope 23, then the images are processed by the image processor 25 (step S1). In this state, the wafers 27 are moved in one direction by the XY stage 22 (step S2).

The image processor 25 detects the continuously moving images for the boundary areas where the luminance shifts from the bright to the dark, and applies the spatial filter to the captured images to enhance the boundary areas where the luminance shifts (step S3). In this embodiment, the boundary of a potential defect appears in the vertical direction of the screen, as shown in FIG. 9; hence, a filter of an n×m size shown in FIG. 10 was used. To be more specific, the size of the filter used was n=5 and m=3. With the filter, no absolute values were obtained, and negative values were all set to zero. The values of "n" and "m" and the values related to the filter are to be properly set according to the conditions of the images of potential defects.

Then, the aforesaid images with enhanced boundaries are subjected to binarization to detect the boundaries so as to obtain clear images of potential defects (step S4). The images of the potential defects with clear contrast are produced, as shown in, for example, FIGS. 11D and 11G. In this embodiment, the boundaries are enhanced, so that a fixed threshold value th=60 was applied.

Subsequently, the characteristic amounts of the detected potential defects are extracted (step S5), true defects and noises are discriminated on the basis of the extracted characteristic amounts to remove the noises (step S6), and only the true defects are counted (step S7).

Next, it is determined whether the inspection on the entire surface has been completed (step S8), and if the determination result is negative, then the program returns to step S1 to repeat the above processing.

Figure 13:
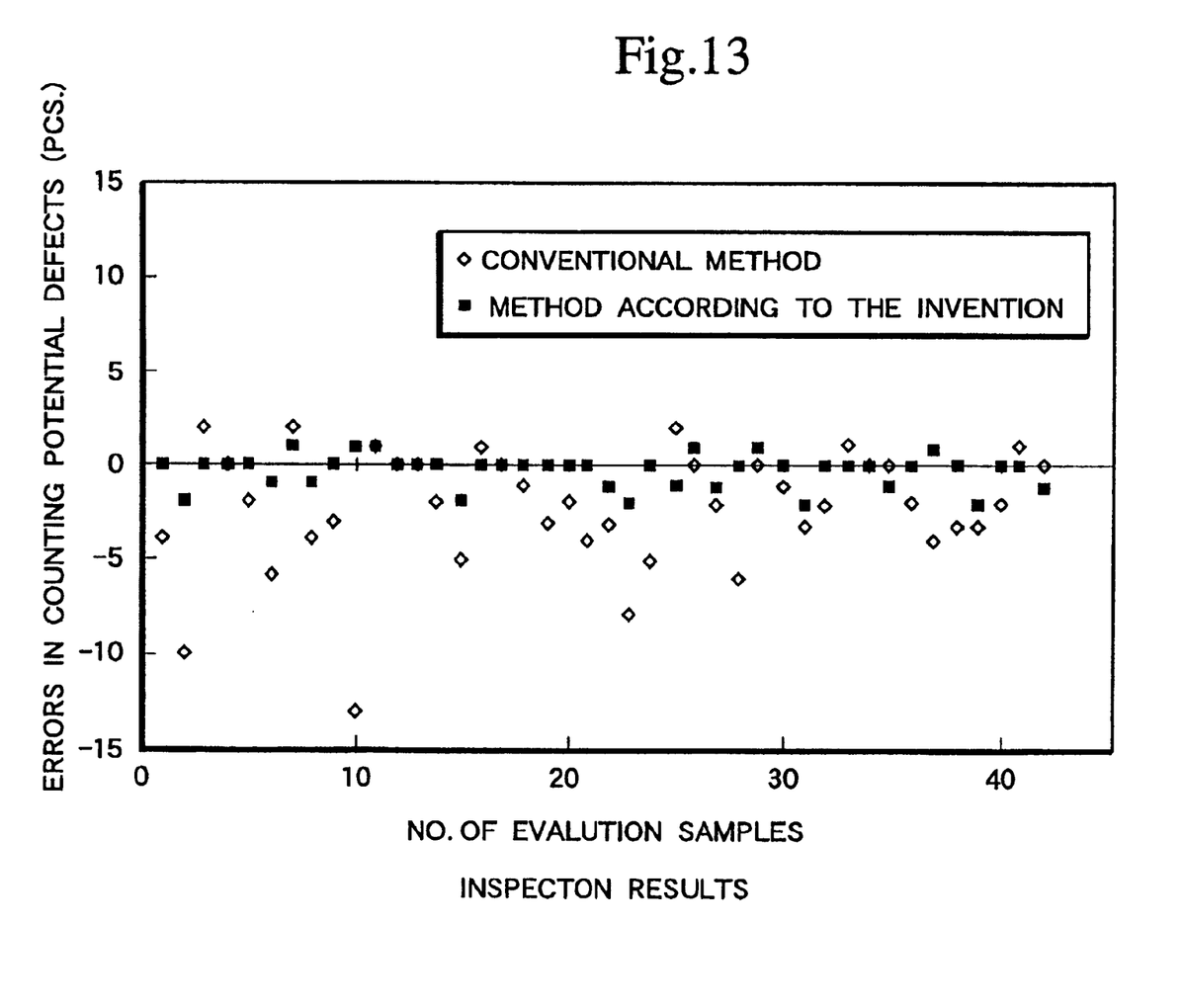
FIG. 13 is a graph comparatively showing the inspection results obtained by the defect inspection method in accordance with the present invention and those obtained by a conventional method.

FIG. 13 shows an example that compares the inspection results obtained by a conventional edge detection technique and the inspection results obtained by applying the processing in accordance with the present invention. The conventional technique tends to count potential defects less than a true number of the potential defects, exhibiting variations in the negative side with respect to correct count. In contrast to this, it can be seen that the processing in accordance with the present invention permits inspection to be performed at the values that are substantially equal to correct values. In this example, 15000 images are captured per sample, and a result exhibiting the largest error was indicated as a representative value. Thus, better results are obtained by processing a larger number of images.

Advantages

As described above, potential defects are identified on the basis of areas where the luminance shifts in captured images rather than capturing one entire potential defect to implement quantitative determination. This arrangement makes it possible to prevent overlapping of the images of potential defects, permitting reduced chances of oversight of potential defects.

The areas where the luminance shifts are enhanced by a spatial filter and binarized to allow images to be captured with better contrast, so that the chances of oversight of potential defects can be reduced, and the overlapping of the images of adjoining potential defects can be restrained, leading to reduced errors in counting potential defects. This makes it possible to achieve more reliable quality assurance and more accurate quality control for objects to be inspected. In addition, the burden on inspectors can be reduced, contributing to labor saving.

Modifications (1) The first and second embodiments have been described, taking silicon wafers as the objects to be inspected; however, the defect inspection method and the defect inspection apparatus in accordance with the present invention are not limited thereto. The defect inspection method and apparatus according to the present invention may be applied to any objects to be inspected that may incur micro defects on the surfaces thereof to obtain the same operations and advantages as those obtained in the first and second embodiments.

(2) In the first embodiment, the set values that provide the evaluation criteria are statistically derived from actual measurements. Alternatively, however, preset values may be used as fixed values. In this case also, the same operations and advantages as those obtained by the aforesaid embodiments can be obtained.

(3) In the second defect inspection method according to the first embodiment, the linear function has been used as the n-order approximate curve. Obviously, however, the approximation may alternatively be implemented using a curve of quadratic function, cubic function or more according to the distribution of potential defects. Appropriate choices should be made according to the distribution of potential defects because the distribution depends upon the contacting situation of tweezers or the like. In this case also, the same operations and advantages as those obtained by the aforesaid embodiments can be obtained.

(4) The first embodiment has been described, taking the OSFs as the examples of defects; however, other types of defects, such as BMDs, can be also inspected in the same manner as that described above.

(5) In the first embodiment, as the defect inspection method using the number and positions of detected potential defects to carry out determination, the descriptions have been given of the examples wherein the density based on one point, the density based on a line, and the density based on the distances between potential defects are used. The present invention, however, is not limited to the above, and may adopt other means using the number and positions of detected potential defects. More specifically, based on the number and positions of the detected potential defects, whether the potential defects are true defects may be determined by another parameter, such as the ratio of the area where the potential defects are concentrated to the entire area.

(6) In the second embodiment, the descriptions have been given, taking the BMDs as the examples of potential defects; however, other types of potential defects, such as OSFs, may be inspected in the same manner as that described above.

(7) In the second embodiment, to detect a change in luminance, the boundary area where the luminance shifts from the bright to the dark has been detected. Obviously, however, a boundary area where the luminance shifts from the dark to the bright may alternatively be detected.

As described in detail above, the defect inspection method and the defect inspection apparatus in accordance with the present invention provide the following advantages:

(1) The density of potential defects is determined on the basis of the number and positions of the detected potential defects according to the methods described above, and the determined density is compared with a set value to decide whether the potential defects are true defects. This arrangement makes it possible to determine more accurately whether the potential defects on a surface of an object to be inspected are true.

As a result, the errors in counting defects can be reduced, making it possible to achieve more reliable quality assurance and more accurate quality control of objects to be inspected.

(2) Defect candidates are identified on the basis of the areas where luminance shifts in captured images, so that overlapping of images of the potential defects can be restrained, and the chances of oversight of the potential defects can be reduced.

(3) The areas where luminance shifts are enhanced by a spatial filter and binarized to produce images of potential defects with high contrast. This arrangement allows the chances of oversight of potential defects to be reduced and the overlapping of the images of adjoining potential defects to be restrained, leading to reduced errors in counting the potential defects.

(4) The advantages described in (2) and (3) above make it possible to achieve more reliable quality assurance and more accurate quality control of the objects to be inspected, and also to reduce the burden on inspecting staff, permitting contribution to labor saving.

What is claimed is:

1. A defect inspection method for detecting potential defects observed on a surface of an object to be inspected, wherein,
    a density of the detected potential defects is determined on the basis of the number of and the positions of the detected potential defects and the positions of the detected defects generated adjacently in dotted or in-line configuration, by using gravity center position of the detected defects as a standard, and the density is compared with a set value so as to decide whether the detected potential defects are true defects.

2. The defect inspection method according to claim 1, wherein
    if it is determined that the detected potential defects are not true defects, then inspection is carried out in a visual field in the vicinity of an inspected visual field.

3. The defect inspection method according to claim 1, wherein the inspection results at two positions that align the gravity center positions of the detected potential defects with the central position of the foregoing area, counts the number of the detected potential defects in the area; determines the density of the detected potential defects on the basis of the ratio of the number of the detected potential defects to the total number of the detected potential defects in the inspection visual field, and decides whether the determined density of the detected potential defects is a set percentage or more so as to determine whether the detected potential defects are true defects.

4. A defect inspection method for detecting potential defects observed on a surface of an object to be inspected, comprising the steps of:

setting an area that is smaller than an inspection visual field if a total number of potential defects in the inspection visual field is smaller than a set value;

aligning the gravity center positions of the detected potential defects with the central position of the foregoing area;

counting the number of the detected potential defects in the area;

determining the density of the detected potential defects on the basis of the ratio of the number of potential defects to the total number of potential defects in the inspection visual field; and deciding whether the determined density of the detected potential defects is a set percentage or more so as to determine whether the detected potential defects are true defects.

5. A defect inspection method for detecting potential defects observed on a surface of an object to be inspected, comprising the steps of:

determining the gravity center positions of all potential defects if a total number of potential defects in an inspection visual field is smaller than a set value;

determining an n-order approximate curve on the basis of the distribution of the gravity center positions;

counting the number of the detected potential defects existing in a set width along the n-order approximate curve;

determining the density of the detected potential defects the basis of the ratio of the number of potential defects to the total number of the detected potential defects in the inspection visual field; and determining whether the density of the detected potential defects is a set ratio or more so as to determine whether the detected potential defects are true defects.

6. A defect inspection method for detecting potential defects observed on a surface of an object to be inspected, comprising the steps of:

determining the gravity center positions of all potential defects if a total number of potential defects in an inspection visual field is smaller than a set value;

calculating the distances among the detected potential defects on the basis of the gravity center positions to determine the mean value of the distances; and determining whether the distance that is smaller than the value obtained by adding or subtracting an offset value preset for the determined mean value is a set ratio or more against the number of combinations of the distances among all potential defects in the inspection visual field so as to determine whether the potential defects are true defects.

7. A defect inspection apparatus for detecting potential defects observed on a surface of an object to be inspected, comprising a defect determining unit, determining a density of the detected potential defects on the basis of the number of and the positions of the detected potential defects and the positions of the detected defects generated adjacently in dotted or in-line configuration, by using gravity center position of the detected defects as a standard, and comparing the density with a set value so as to decide whether the detected potential defects are true defects.

8. The defect inspection apparatus according to claim 7, wherein if the defect determining unit determines that the detected potential defects are not true defects, then performs inspection in a visual field in the vicinity of an inspected visual field.

9. The defect inspection apparatus according to claim 7, wherein the defect determining unit compares the inspection results at two positions that are symmetrical on the whole surface of an inspected object, and determines whether the difference there between exceeds a set value so as to determine whether the detected potential defects are true defects.

10. A defect inspection apparatus for detecting potential defects observed on a surface of an object to be inspected, comprising a defect determining unit, wherein the defect determining unit sets an area that is smaller than an inspection visual field if a total number of potential defects in the inspection visual field is smaller than a set value, aligns the gravity center positions of the potential defects with the central position of the area, detects the number of potential defects in the area;

determines the density of the potential defects on the basis of the ratio of the number of the detected potential defects in the area to the total number of potential defects in the inspection visual field, and decides whether the determined density of the potential defects is a set percentage or more so as to determine whether the detected potential defects are true defects.

11. A defect inspection apparatus for detecting potential defects observed on a surface of an object to be inspected, comprising a defect determining unit, wherein the defect determining unit determines the gravity center positions of all potential defects if a total number of potential defects in an inspection visual field is smaller than a set value, determines a curve on the basis of the distribution of the gravity center positions, detects the number of potential defects existing in a set width along the n-order approximate curve, determines the density of the potential defects on the basis of the ratio of the number of the detected potential defects to the total number of potential defects in the inspection visual field, and determines whether the density of the potential defects is a set ratio or more so as to determine whether the detected potential defects are true defects.

12. A defect inspection apparatus for detecting potential defects observed on a surface of an object to be inspected, comprising a defect determining unit, wherein the defect determining unit determines the gravity center position of all potential defects if a total number of potential defects in an inspection visual field is smaller than a set value, calculates the distances among the potential defects on the basis of the gravity center positions to determine the mean value of the distances, and determines whether the distance that is smaller than the value obtained by adding or subtracting an offset value preset for the determined mean value is a set ratio or more against the number of combinations of the distance among all potential defects in the inspection visual field so as to determine whether the potential defects are true defects.

13. A defect inspection method for capturing, by using a differential interference microscope, a surface of an object to be inspected, and processing an image to count the number of potential defects observed on the surface, comprising the steps of:

applying a spatial filter to the captured image to enhance the spot where the luminance shifts;

binarizing the enhanced spots;

detecting potential defects at the binarized and enhanced spots where luminance shifts in the captured image;

determining whether the detected potential defects are true defects or noises based on the characteristic amount of the detected spots; and counting the number of true defects.

14. A defect inspection apparatus for capturing, by using a differential interference microscope, a surface of an object to be inspected, and processing an image to count the number of potential defects observed on the surface, comprising:

a boundary enhancing unit that applies a spatial filter to the captured image to enhance a boundary area where luminance changes, and binarizes the boundary area to obtain a clear potential defect image;

a defect detecting unit for detecting the potential defects that have been enhanced and clarified by the boundary enhancing unit; and a defect counting unit that determines whether the detected potential defects are true defects or noises on the basis of the characteristic amount of the area detected by the defect detecting unit, then counts the number of true defects.

* * * * *